United States Patent
Malzl

(10) Patent No.: US 10,631,658 B2
(45) Date of Patent: Apr. 28, 2020

(54) MATTRESS

(71) Applicants: DESCANSARE SLEEP LAB S.L., Logrono (ES); Hans Malzl, Salzburg (AT)

(72) Inventor: Hans Malzl, Salzburg (AT)

(73) Assignees: Hans Malzl, Salzburg (AT); DESCANSARE SLEEP LAB S.L., Logrono (ES)

( * ) Notice: Subject to any disclaimer, the term of this patent is extended or adjusted under 35 U.S.C. 154(b) by 0 days.

(21) Appl. No.: 15/113,842

(22) PCT Filed: Jan. 21, 2015

(86) PCT No.: PCT/EP2015/051080
§ 371 (c)(1),
(2) Date: Jul. 25, 2016

(87) PCT Pub. No.: WO2015/110448
PCT Pub. Date: Jul. 30, 2015

(65) Prior Publication Data
US 2016/0338500 A1    Nov. 24, 2016

(30) Foreign Application Priority Data

Jan. 23, 2014 (DE) .................... 20 2014 100 278 U

(51) Int. Cl.
*A61B 5/00* (2006.01)
*A47C 27/08* (2006.01)
(Continued)

(52) U.S. Cl.
CPC ............ *A47C 27/083* (2013.01); *A47C 21/04* (2013.01); *A47C 27/082* (2013.01); *A47C 27/10* (2013.01); *A47C 31/123* (2013.01); *A61B 5/6892* (2013.01)

(58) Field of Classification Search
CPC ... A47C 27/083; A47C 31/123; A47C 27/082; A47C 27/10; A61B 5/6892
See application file for complete search history.

(56) References Cited

U.S. PATENT DOCUMENTS 6,421,858 B1 * 7/2002 Cuerel ................. A47C 27/082
5/710
2003/0221261 A1 * 12/2003 Torbet ................. A47C 27/082
5/713
(Continued)

FOREIGN PATENT DOCUMENTS

CN       103431846       12/2013
DE      102004041996       3/2006
(Continued)

OTHER PUBLICATIONS

IPER for the parent PCT application, mailed on Jul. 26, 2016.

*Primary Examiner* — Eric D. Bertram
(74) *Attorney, Agent, or Firm* — Graeser Associates International, Inc.; D'Vorah Graeser

(57) ABSTRACT

The invention relates to a mattress (110) made of elastic foam or rubber material and comprising individually controllable air chambers (120, 120a) that are inserted in the transverse direction and are equipped with at least one pressure measurement sensor, the pressure in the air chambers (120, 120a) being adjustable based on an algorithm which is used by a control device and which correlates with sleep quality calculations also made by the control device and/or which follows the principle of the changing pressure sensed. The invention also relates to a corresponding method.

25 Claims, 1 Drawing Sheet

Figure 1:
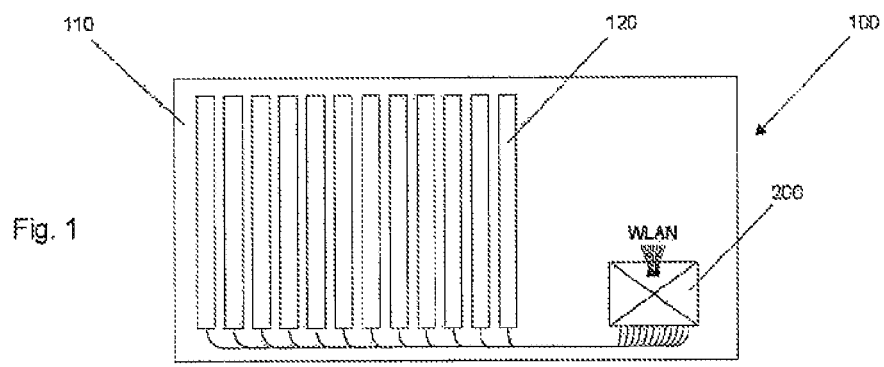

(51) Int. Cl.
*A47C 27/10* (2006.01)
*A47C 31/12* (2006.01)
*A47C 21/04* (2006.01)

(56) References Cited

U.S. PATENT DOCUMENTS

2010/0318239 A1* 12/2010 Oexman ............ A47C 23/0433
 700/301
2011/0010014 A1* 1/2011 Oexman .............. A47C 27/061
 700/276

FOREIGN PATENT DOCUMENTS

| WO | 2009102361 | 8/2009 |
| WO | 2009108228 | 9/2009 |

* cited by examiner

MATTRESS

The invention relates to a mattress made of foam material, for example made of latex or a cellular material, with air chambers that are incorporated transversely, the inner pressure of which can be measured, and where appropriate, be modified individually for the purpose of achieving different lying physiological and therapeutic effects. Activation takes place through a control device integrated in the mattress, referred to as the technical box, which is connected through a LAN or WLAN connection to an Internet server or a local computer and obtains functionally relevant information.

One of the essential functions is the capacity of the mattress according to the invention to adapt, by means of automatic learning intelligence, to the support profile that leads to an optimized sleep and lying result. This automatic learning intelligence is referred to herein as an ergomatic function. In this regard, sleep is recorded throughout the entire nighttime rest in the form of pressure measurements at specific points of the body, and sleep quality is evaluated according to an algorithm. The so-called sleep quality index, SQI, is calculated in this sense.

An additional algorithm triggers modifications in the support structure of the mattress, the effects of which are evaluated again, such that the system continues with this systematic sampling mode in the event of improved sleep quality, or makes another attempt and repeats the process in the event of a worse result until it actually achieves the highest sleep quality possible.

An additional function is the so-called pressure change function which, following the "effect of change sensed" phenomenon, slightly modifies time and time again the support profile of the mattress at time intervals that the user of the mattress must choose, such that stimulating influences on nervous pathways are temporarily released, and this gives the user the advantage of permanently counteracting pains and other acute symptoms. The "effect of change sensed" is based on the fact that in the event of modifying the lying position or modifying the support profile of the mattress, the spinal nerves starting in the spinal column are not constantly exposed to pressure, but rather it is likewise modified or displaced with a slight modification of the support structure of the mattress. Therefore, the spinal nerves, the stimulation of which is incidentally responsible for backaches occurring when lying down, experience a changing mechanical load, such that before becoming acute symptomatology in each case, it can be prevented by displacing the influence of the pressure to other areas of the spinal column. In the event of elderly people susceptible to an accordingly higher stimulation, this effect of change must be carried out in shorter intervals. In this regard, the actual user can choose the time interval of these modifications in the support profile of the mattress, choosing from among the different options that are offered.

Based on the viewpoint that an individually user-adapted mattress leads to better sleep and rest, inventors and manufacturers have recently dedicated themselves to making customizable mattresses. Despite the possible advantages that mattresses of this type may entail for health, it is difficult to ergonomically determine their correct support profile and to assure it over prolonged periods of use, which is complicated not just by the wear of the material but also by the body modifications of the user.

The use of air as a bearing and regulating element was already implemented by many builders and manufacturers when so-called inflatable mattresses, which are no longer single-chamber concepts, but rather also multi-chamber concepts today, were launched on the market. In this regard, only a limited and somewhat imprecise individual adaptation was possible, and in such case, maintenance of an ideal support structure depended on the action of the user, who as a general rule, however, has neither sufficient technical training nor sufficient experience to act in a targeted and satisfactory manner.

In the field of individual mattresses, the regulation of which is not by means of air chambers but rather by means of layers of cellular material, even though assistance services are offered and used in practice, such that the user of the mattress systematically receives instructions from professional consultants to achieve an optimal lying result, it is the user who has to make the physical modification to the mattress, which requires opening the mattress and changing individual support elements. This may at times be difficult, particularly for elderly people.

The present invention solves all these problems by having the mattress obtain the support profile by means of air chambers with a different filling that are closely lined up one next to another, instead of by means of support layers, and subsequently being able to be modified without user intervention. On one hand, this is done such that the user (as in the case of individual mattresses made of cellular material) can avail of a professional assistance service that communicates with the user and analyzes and evaluates the lying results achieved, but the modifications that must accordingly be made to the support profile of the mattress must not be made by the user, but rather the consultant can transmit them directly to the mattress through an Internet connection, such that the support profile is changed accordingly. Additionally, according to the invention, instead of allowing a consultant to indicate an optimal lying result, the user has the possibility of leaving this improvement process directly up to the mattress, so as not to waste time that would otherwise have to be dedicated to communicating with a consultant.

An additional innovation of the mattress according to the invention is a sleep monitoring function, which records, evaluates and documents the entire progress of sleep. To that end, pressure sensors are incorporated, particularly in the air feeding conduits to the air chambers, which take a permanent measurement of the pressure acting on specific air chambers, such that based on an algorithm, the control device (which can be located both inside and outside the mattress) determines when changes to the user's lying position (lying on their side, lying on their back or lying on their stomach) take place, how often these changes take place during nighttime rest and which lying positions were adopted in each case. This sleep monitoring is the basis for calculating the sleep quality, or SQI, which is likewise done by the control device by means of its proprietary algorithm.

In an additional embodiment of the invention, preferably flat, highly sensitive pressure sensors are additionally incorporated inside the mattress in the area of the rest surface, i.e., on the upper part in a use situation. This provides the basis for additional properties of the mattress according to the invention not previously used in mattresses or in other consumer goods.

In this sense, according to the invention warning devices that warn the user of health issues are provided. These health issues particularly refer to the phenomenon of sleep apnea as well as other early-stage health problems which can be recognized based on heart and breathing activity measurements with the aid of the highly sensitive pressure sensors in the area of the rest surface of the mattress and the comparison of said measurements with comparative standards previously stored in the computer.

Therefore, based on these heart and breathing measurements, algorithms can be used which, acting as a "home" sleep lab, identify both deep and REM sleep stages, and in this regard the number, time and duration of sleep apnea episodes are determined in order to trigger the corresponding alarm in the event of exceeding a limit value that can be predetermined.

Other algorithms make it possible to differentiate normal heart and breathing activity values from anomalous values (which are stored in the computer or in the server in the form of comparative standards), and in the event of exceeding a limit value they also trigger an alarm. Therefore, the idea of early detection of a disease or illness is conveyed to the home environment of humans for the first time ever, using the signals given off by the body, every night and in bed in the sense of a permanent observation, which are associated with corresponding warning functions for an early warning health care device.

Particularly, in this sense it is additionally envisaged that the highly sensitive pressure sensors located in the mattress detect mechanical pressure pulses in the form of micro-oscillations, such as those generated by the heartbeat and the breathing of the person on the mattress. The heartbeat frequency, intensity, intensity oscillations, and rate, for example, can thereby be detected by these highly sensitive pressure sensors. Mechanical pressure pulses induced by breathing in the torso area can also be recorded with these pressure sensors. In each case, these pressure pulses result in pressure profiles, which are significant for breathing or heartbeat and are compared with at least one pressure profile stored at a previous time, and/or pressure profile that can be predetermined. By means of this comparison between the stored pressure profile and the actual pressure profile, information can be obtained about if normal function exists, or of there is a significant deviation, which allows deducing the possible development of a disease or illness, such that activation of a function, for example an alarm function, takes place.

In a study created particularly for this purpose by the inventor, the accumulated comparative standards, specifically pressure profiles, were divided up into categories in order to be able to differentiate between different clinical pictures. Furthermore, suspicious events can also be split up such that they direct the suspicion in a specific health risk direction, for example, there could be a risk of a stroke, myocardial infarction, cancer, diabetes, etc. Therefore, the alarm function can also be transmitted in the form of a notice, for example, directly and automatically to the primary care physician by means of an email in order to give said physician the chance to analyze and evaluate possible suspicious events by means of a medical evaluation page associated with the patient in order to accordingly advise, where appropriate, the user of the mattress (i.e. the physician's patient) to undergo a more thorough medical examination.

The pressure pulses provided by the mattress with respect to breathing activity are preferably related to the aid of a proprietary algorithm with the micro-oscillations provided by the heartbeat, such that based on these two measurement magnitudes, similarly to navigation positioning, a third measurement magnitude can be determined, the informative value of which is greater than that of the individual measurement magnitudes considered separately. Also in this case, these measurement magnitudes established by means of positioning methods are processed to give a profile standard which is compared with at least one comparative standard (i.e. pressure profile) established according to the same method in the study and stored at a previous time, and/or a pressure profile that can be predetermined, and in the event of a significant deviation the activation of a function, for example a warning function, in turn takes place.

This positioning method is optionally enhanced in one or several measurement magnitudes, for example in a temperature value and in biochemical values, such that in this case based on a proprietary algorithm more than two measurement magnitudes, specifically the measured heart activity, breathing activity, body temperature and biochemical value magnitudes (obtained for example by means of temperature sensors and/or moisture sensors) result in an additional measurement magnitude, the informative value of which is not only greater than that of the individual measurement magnitudes considered separately, but also is greater than that achieved in the positioning method with only two starting measurement magnitudes.

It can also be envisaged that the pressure profiles determined with the aid of pressure sensors are evaluated using medical diagnostic software in order to establish if there is possibility a pathological modification to behavior of the person located on the mattress during sleep.

In an additional embodiment of the invention, at least one highly sensitive temperature sensor measuring body temperature is additionally incorporated inside the mattress preferably in the area of the rest surface, i.e., in the upper part of the mattress. Furthermore, in this embodiment there can be incorporated inside the mattress, preferably on the upper surface thereof, thin capillary tubes, which are filled with a liquid, preferably water, which is heated or cooled, as needed, by means of module located outside or inside the mattress. In the event of increased body temperature, which allows inferring a pathological state, the computer in the technical box of the mattress or that of the server, predetermines if the mattress should be heated and for how long. The body of the user of the mattress therefore experiences, similarly to the healthy effect of a hot water bag, as a result of the mattress, a support with thermal energy that will help the user get over the illness more quickly. Once the body reaches normal temperature again, the mattress is likewise set to the normal temperature again. Optionally, the system activates an alarm function in the event of exceeding normal body temperature.

The method for determining body temperature or for determining that the normal value has been exceeded is based on the system of the mattress taking permanent temperature measurements, and the average of said measurements is used to determine normal body temperature by means of an algorithm. The uncertainty factor resulting from the fact that each body has a different body temperature in relation to the surrounding environment (i.e., that which is used to cover up, the material of the mattress, clothing and ambient temperature), can therefore be excluded. An average temperature value calculated over a prolonged period accordingly forms the calculation basis for determining normal body temperature, such that based on this normal value, it can be determined at a later time that normal body temperature has been exceeded, and it is also possible to determine the incremental value of this exceeding.

In an additional embodiment of the invention, additional highly sensitive moisture sensors are included inside the mattress, preferably in the area of the rest surface, i.e. in the upper part of the mattress, with the aid of which the system can, through the moisture given off by the body (i.e., sweat), provide information with respect to biochemical parameters, which in turn are indicators of a specific state of health.

These parameters can be integrated in the elaboration of comparative standards and additionally provide additional measurement values for the positioning method described above.

The invention is described in further detail below by means of non-limiting embodiments in reference to the corresponding drawings.

FIG. 1 shows a device 100 according to the invention with air chambers 120 lined up one next to another that are incorporated in the transverse direction in the mattress 110, which are controlled by a control device 200 for the purpose of filling with air. In this sense, the pressure sensors required to that end are arranged in the control unit 200. A LAN or WLAN connection transmits the orders to that end.

Figure 2:
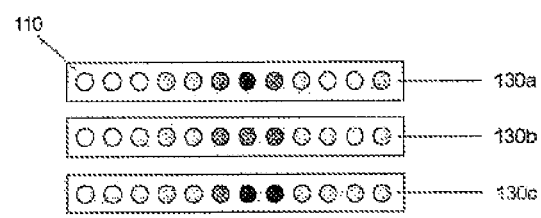

FIG. 2 shows three different support or pressure profiles 130a, 130b, 130c of the mattress 110, as they are automatically formed by the mattress 110, for example, in the case of the pressure change function in a fixed sequence accordingly.

Figure 3:
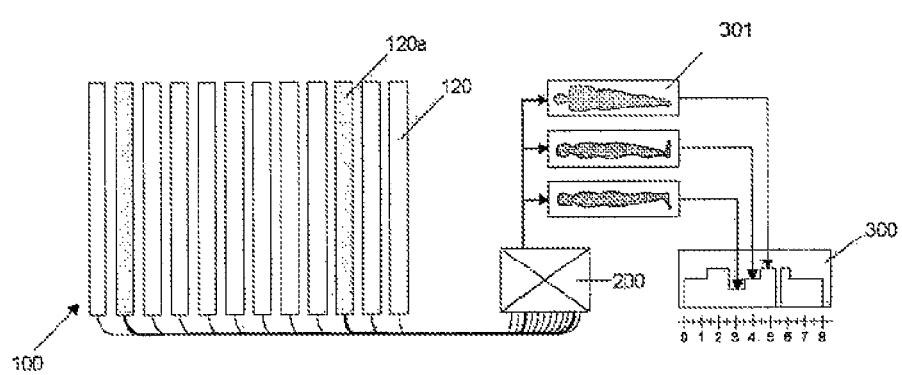

FIG. 3 shows a schematic depiction of the method according to the invention with the sleep monitoring function. The individual air chambers 120 can be seen, two of which air chambers 120a in the depicted variant of the invention take permanent measurement of the air pressure inside the air chamber 120a. The pressure values measured in this respect are transmitted to the control device 200 which makes a comparison in the different lying positions 301 by means of a lying profile 300 previously established by the user of the mattress, and it can thereby determine the lying position 301 adopted at the respective time.

Figure 4:
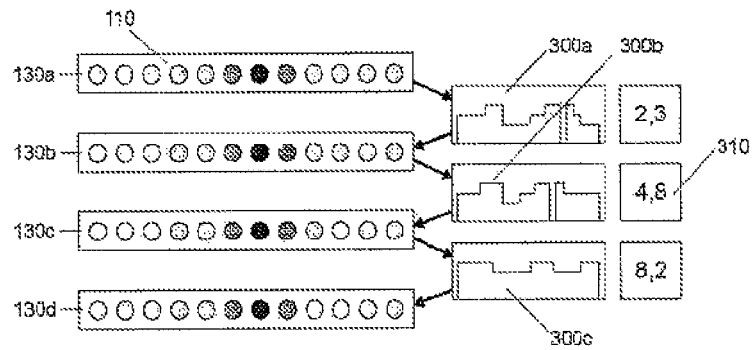

FIG. 4 shows a schematic depiction of the method according to the invention with ergomatic function, in which the mattress 110 controlled according to an algorithm modifies its support or pressure profile 130a, 130b, 130c, 130d on a small scale, then sleep quality is evaluated through the lying profiles 300a, 300b, 300c detected, and it is accordingly evaluated whether or not the modification of the support profile 130a, 130b, 130c, 130d has led to improved sleep quality. This improved sleep quality is provided in the form of a number value 310, the so-called sleep quality index (SQI), which through the algorithm is related to the variation of the user position. This knowledge activates an additional modification to the support profile 130a, 130b, 130c, 130d, and the operation is repeated until maximum sleep quality is achieved.

Figure 5:
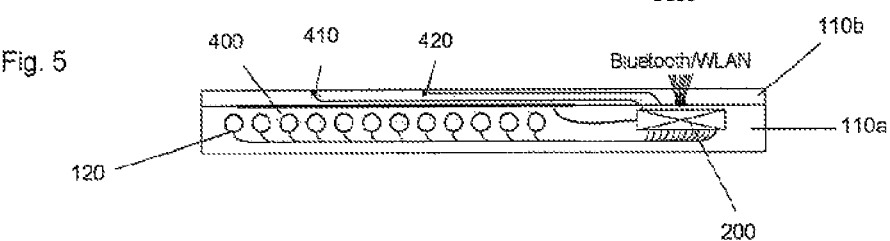

FIG. 5 depicts an additional embodiment of the invention, in which the mattress 110 according to the invention has air chambers 120 in a lower mattress part 110a, the inner pressure of which chambers 120 can be modified as described above to obtain the support profile 300 required for optimal sleep quality. In an upper mattress part 110b forming the rest surface there is arranged a flat pressure measurement device 400 which is made up of a large number of highly sensitive pressure measurement sensors which can detect the micro-oscillations generated by the breathing and the heartbeat of a person lying on the mattress 110 and transmit them through the control device 200 directly or through a smart phone, tablet or other computer device to an Internet server, the pressure pulses being able to be transmitted through WLAN or Bluetooth, for example.

Additionally, in this embodiment of the invention, in the upper mattress part 110b there are arranged additional sensors, specifically a temperature sensor 410 and a moisture sensor 420, which are used to detect parameters such as body temperature, or biochemical parameters, such as those used by the algorithms for early disease detection.

The invention claimed is:

1. A mattress comprising a comfort layer and a support layer, wherein said comfort layer is made of a foam or rubber material, has no air chambers therein, and is non-integral to and is situated over said support layer; wherein said support layer is made of an elastic foam; wherein said support layer comprises a plurality of air chambers and a control device; wherein the said plurality of air chambers are individually controllable air chambers that are embedded within the elastic foam of said support layer in the transverse direction over the width direction of the mattress, have elongated tube shape, and provide support to the mattress; wherein said control device comprises a plurality of pressure measurement sensors and an ergomatic function; wherein the ergomatic function is adapted to a process of modifying a support or pressure profile on a small scale, analyzing a lying profile detected by said pressure measurement sensors connected to said air chambers, calculating a sleep quality that is provided in the form of a number value that is related to variation in user position, comparing the calculated sleep quality to a previous sleep quality to determine whether or not the modification of the said support profile has improved sleep quality, and repeating the process until maximum sleep quality is achieved.

2. The mattress according to claim 1, characterized in that the control device is connected to the Internet.

3. The mattress according to claim 1, characterized by at least one additional pressure measuring device which is arranged in the area of a rest surface of the mattress and is preferably flat, where said pressure measuring device detects mechanical pressure pulses in the form of micro-oscillation, such as those generated by the heartbeat and the breathing of the person on the mattress.

4. The mattress according to claim 1, characterized in that the control device is connected over the Internet with at least one data exchange server.

5. The mattress of claim 1, wherein the control device is arranged inside the support layer of the mattress.

6. The mattress of claim 1, wherein said comfort layer contains sufficient thickness to incorporate a plurality of sensors without interfering the comfort of the user, preferably from 1 to 3 inches in thickness, where the thickness does not exceed 25 percent of the mattress.

7. The mattress of claim 1, wherein the mattress further comprises a module for heating and cooling a liquid, where said module communicates with said control device.

8. The mattress of claim 7, wherein said comfort layer comprises a plurality of sensors and capillary tubes for holding the liquid.

9. The mattress of claim 8, wherein the plurality of sensors are temperature sensors and moisture sensors, where both types of sensors communicate with said control device to regulate the temperature of the mattress by heating or cooling the liquid inside of said capillary tubes.

10. The mattress of claim 1, wherein said comfort layer comprises a plurality of highly sensitive pressure sensors, of temperature sensors, and of moisture sensors.

11. A method for adjusting the pressure in the air chambers of a mattress comprising a comfort layer and support layer, wherein said comfort layer is made of a foam or rubber material, has no air chambers therein, and is non-integral to and is situated over said support layer, wherein said support layer is made of an elastic foam, wherein said support layer comprises a plurality of air chambers and a control device, wherein the said plurality of air chambers are individually controllable air chambers that are embedded within the elastic foam of said support layer in the transverse direction over the width direction of the mattress, have elongated tube shape, and provide support to the mattress, wherein said control device comprises a plurality of pressure measurement sensors and an ergomatic function, wherein the ergomatic function is adapted to a process of modifying a support or pressure profile on a small scale, analyzing a lying profile detected by said pressure measurement sensors connected to said air chambers, calculating a sleep quality that is provided in the form of a number value that is related to variation in user position, comparing the calculated sleep quality to previous sleep quality to determine whether or not the modification of the said support profile has improved sleep quality, and repeating the process until maximum sleep quality is achieved.

12. The method according to claim 11, further comprising obtaining data for the control device from at least one server through an Internet connection.

13. The method according to claim 11, further comprising recording pressure profiles by means of pressure measurement sensors over a period of time of nighttime rest and evaluating said pressure profiles to determine if the person lying down is in a specific lying position, such as lying on their side, lying on their back or lying on their stomach.

14. The method according to claim 13, characterized in that the assignment of the determined lying positions takes place over time both in relation to modification of the position and to duration of the lying position adopted in each case.

15. The method according to claim 11, further comprising storing pressure profiles of a respective user of the mattress.

16. The method of claim 11, further comprising monitoring a person's state of health during nighttime rest and early detection of a diseases by using sensors to detect parameters such as body temperature, biochemical parameters, or combination of both and by using the control device that receives said parameters and compares said parameters to known values for early disease detection.

17. A method for evaluating pressure pulses which are recorded by additional highly sensitive pressure sensors arranged in a mattress comprising a comfort layer and support layer, wherein said comfort layer is made of a foam or rubber material, has no air chambers therein, and is situated over said support layer, wherein said comfort layer comprises a plurality of highly sensitive pressure sensors, of temperature sensors, and of moisture sensors, wherein said support layer is made of an elastic foam, wherein said support layer comprises a plurality of air chambers and a control device, wherein the said plurality of air chambers are individually controllable air chambers that are embedded within the elastic foam of said support layer in the transverse direction over the width direction of the mattress, have elongated tube shape, and provide support to the mattress, wherein said control device comprises a plurality of pressure measurement sensors and an ergomatic function, wherein the ergomatic function is adapted to a process of modifying a support or pressure profile on a small scale, analyzing a lying profile detected by said pressure measurement sensors connected to said air chambers, calculating a sleep quality that is provided in the form of a number value that is related to variation in user position, comparing the calculated sleep quality to previous sleep quality to determine whether or not the modification of the said support profile has improved sleep quality, and repeating the process until maximum sleep quality is achieved, the method characterized in that a current pressure pattern is established based on the pressure pulses, this current pressure profile is compared with at least one pressure pattern established at a previous time, and in the event of a deviation with respect to a value or interval of values that can be predetermined, a function is activated.

18. The method according to claim 17, characterized in that the activation of the function is a warning function.

19. The method according to claim 17, characterized in that the activation of the function is a modification of the pressure in air chambers of the mattress for achieving a modification of the support function of the mattress for a person located on same.

20. The method according to claim 17, characterized in that the current body temperature actual of a person located on the mattress is calculated through at least one temperature sensor, in which the current body temperature actual is then compared with a determined normal body temperature based on a long-term measurement at a previous time.

21. The method according to claim 20, characterized in that in the event of the current body temperature deviating from the normal body temperature, particularly in the event of a temperature increase, regulation of the temperature of the mattress take place through a temperature regulation device.

22. The method according to claim 20, characterized in that in the event of the current body temperature deviating from the normal body temperature, a warning function is activated.

23. The method according to claim 17, wherein a measured pressure value is related to at least another pressure value of the pressure sensor incorporated in the mattress, and the value thereby generated results in a new and third measurement magnitude thereby having greater informative value.

24. The method according to claim 23, characterized in that the third measurement magnitude obtained is related with a measured value of a temperature sensor.

25. The method according to claim 23, characterized in that the third measurement magnitude obtained is related with a measured value of a moisture sensor.

* * * * *